United States Patent [19]

Brion et al.

[11] Patent Number: 5,409,952
[45] Date of Patent: Apr. 25, 1995

[54] HETEROCYCLIC COMPOUNDS: 2-STYRYL-4H-1-BENZOPYRAN-4-ONES

[75] Inventors: Jean D. Brion, Saint-Leu La Foret; Guillaume Le Baut, Saint-Sebastien Sur Loire; Francoise Zammatio, Nantes; Alain Pierre, Marly Le Roi; Ghanem Atassi, Saint Cloud; Larbi Belachmi, Nantes, all of France

[73] Assignee: Adir et Compagnie, Courbevoie, France

[21] Appl. No.: 143,916

[22] Filed: Oct. 27, 1993

Related U.S. Application Data

[62] Division of Ser. No. 987,166, Dec. 8, 1992, abandoned, which is a division of Ser. No. 691,746, Apr. 26, 1991, abandoned.

[30] Foreign Application Priority Data

Apr. 27, 1990 [FR] France .................. 90 05360

[51] Int. Cl.⁶ ............................................. A61K 31/35
[52] U.S. Cl. .................................... 514/455; 549/387
[58] Field of Search .................. 549/387; 514/455; 548/526; 546/197, 270; 544/150, 60

[56] References Cited

U.S. PATENT DOCUMENTS

4,148,900 4/1979 Doria et al. ................. 549/401
4,177,286 12/1979 Doria et al. ................. 514/456

OTHER PUBLICATIONS

Kossakowski, et al., Acta Polon, Pharm.XLIV, Nr 2, 1987, "Synteza Aminoetylowych 1 Aminoalk-anolowych Pochodnych 7-Styryl-5H-Furo[3,2-g] [1] Benzopiran-5-onu", pp. 147–154.

Kossakowski, Acta Polon, Pharm. XXXVII, Nr 6, 1980, "Synthesis of [2-styryl-8-methoxyfuran(3':-2'-6:7)chromonoxy-5]propionic acid and its derivatives", pp. 625–629.

Musante, et al., Am. Chim., 45, (1955), "Su alcuni nuovi derivati della Khellina e del suo prodotto di demetilazione.", pp. 918–942.

El-Sharief, et al., Egypt. J. Chem. 27, No. 4, (1984), "Synthesis of some visnagin derivatives with expected biological activity", pp. 533–546.

Regaila, et al., Egypt. J. Pharm. Sci. vol. 30, No. 1-5, (1989), "Reactions with Visnagin and Khellin. Synthesis and biological activity of some 5-substituted-furobenzopyran and 2-styryl furochromone derivatives", pp. 159–170.

Sidky, et al., J. Chem. U.A.R., 11, No. 3, (1968), "On 2-styrylvisnagin and 2-styrylkhellin", pp. 393–395.

*Primary Examiner*—Nicky Chan
*Attorney, Agent, or Firm*—Gordon W. Hueschen

[57] ABSTRACT

A compound of the formula (I)

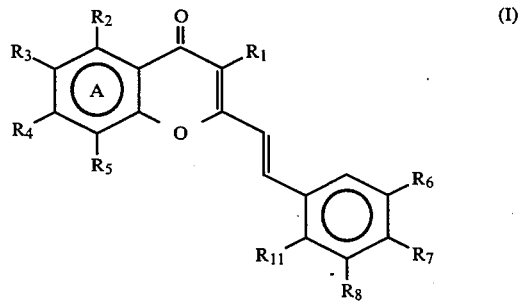

in which:

$R_1$ represents a hydrogen atom, a lower alkyl group, a hydroxy group or a lower alkoxy group, $R_2$, $R_3$, $R_4$, $R_5$, $R_6$, $R_7$, $R_8$ and $R_{11}$ are as defined in the description.

Medicaments.

5 Claims, No Drawings

HETEROCYCLIC COMPOUNDS: 2-STYRYL-4H-1-BENZOPYRAN-4-ONES

The present application is a division of our application Ser. No. 07/987,166, filed Dec. 8, 1992, now abandoned, which in turn is a division of our application Ser. No. 07/691,746, filed Apr. 26, 1991, now abandoned.

The present invention relates to new compounds having anti-cancer properties belonging to the 2-styryl-4H-1-benzopyran-4-one family.

Compounds from the same family are known, but for their anti-allergic properties. Patents BE 885319, BE 855657 and BE 869407 describe compounds of that structure with the 3-position occupied by an alkyl group and the 6-position occupied by a carboxy (or carboxylate) group, which are claimed as inhibitors of allergic symptoms.

More particularly, patent EP 237166 describes the cytotoxic properties of a 2-styrylchromone, hormothamnione, isolated from an alga.

Therapeutic needs demand the constant development of new anti-cancer drugs with the aim of obtaining molecules that are both more active and also less toxic and, if possible, act according to original mechanisms.

The compounds of the present invention are distinguished not only by their cytotoxic properties but also by their cell-differentiating properties, indicating possible therapeutic use as anti-cancer drugs;

The present invention relates more especially to molecules of the general formula:

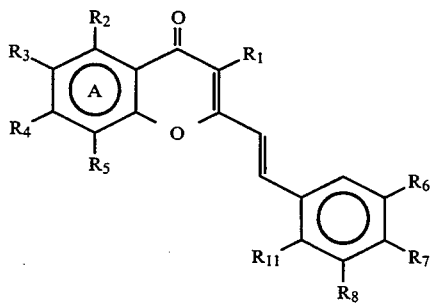

in which:

$R_1$ represents a hydrogen atom, a lower alkyl group, a hydroxy group or an alkoxy group, $R_6$, $R_7$, $R_8$ and $R_{11}$ which may be the same or different, each represents, independently of the others, a halogen, hydroxy, lower alkoxy, thio, lower alkylthio, sulphonyl or lower alkylsulphonyl group or a group of formula (G):

$$D-(A)_m-(O-CO)_p-(B)_n \qquad (G)$$

in which n, m and p, which may be the same or different, are equal to 0 or 1, with the proviso that when p=0, m=0;

or $R_8$ and $R_{11}$ together with the aromatic ring carrying them from a naphtyl group, A and B, which may be the same or different, represent a linear or branched lower alkyl group or a linear or branched lower alkenyl group;

D represents a hydrogen atom or a group of the formula:

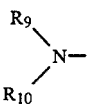

in which $R_9$ and $R_{10}$, which may be the same or different, each represents, independently of the other, a hydrogen atom, a lower alkyl group or a lower alkyl-acyl group, or $R_9$ and $R_{10}$, together with the nitrogen atom carrying them, form a mono- or bi-cyclic nitrogen-containing heterocyclic system having from 4 to 10 apices among which there may be one or two hetero atoms selected from oxygen, sulphur and nitrogen;

each of $R_2$, $R_3$, $R_4$ and $R_5$, which may be the same or different, represents a halogen atom, a hydroxy group, a lower alkoxy group or a group of formula (G) as defined hereinbefore, with the proviso that:

at least one of $R_3$ and $R_5$ represents a group of formula (G) other than hydrogen, if $R_3$ represents a group of formula (G) in which n=0 and p=1, then at least one of $R_2$, $R_4$ and $R_5$ is other than hydrogen, if $R_5$ represents a methyl group or if $R_3$ represents a lower alkyl group, then at least one of the other three substituents of the aromatic ring A is other than hydrogen, or $R_3$ and $R_4$ together with the aromatic ring carrying them form a saturated or unsaturated, bi or tri-cyclic system having from 9 to 15 atoms capable of including in a carbon skeleton one or more hetero atoms selected from oxygen, sulphur and nitrogen, with the proviso that, when $R_3$ and $R_4$ together with the aromatic ring carrying them form a saturated or unsaturated benzofuran or benzopyran system, $R_2$ and $R_5$ cannot represent a lower alkoxy or hydroxy group when $R_6$, $R_7$, $R_8$ and $R_{11}$ simultaneously represent a hydrogen atom, and when $R_3$ and $R_4$ together with the aromatic ring carrying them form an ungaturated benzofuran system, $R_7$ cannot represent a lower alkyl group when $R_6$, $R_8$ and $R_{11}$ simultaneously represent a hydrogen atom, $R_2$ a lower alkoxy group and $R_5$ a hydrogen atom or a lower alkoxy group, their isomers (the configuration around the double bond may be E or Z, preferentially E), enantiomers, diastereoisomers and also, when the molecule comprises an acidic group, their addition salts with a pharmaceutically acceptable base and, when the molecule contains a basic group, their addition salts with a pharmaceutically acceptable acid, there being understood by lower alkyl, lower alkenyl and lower alkoxy groups linear or branched groups comprising from 1 to 6 carbon atoms.

Of the bases capable of forming salts with compounds of formula (I) in which R represents a carboxy group there may be mentioned by way of example sodium, potassium, calcium and aluminium hydroxides, alkali metal and alkaline earth metal carbonates, and organic bases, such as triethylamine, benzylamine, diethanolamine, tert.-butylamine, dicyclohexylamine, arginine etc.

Of the acids capable of forming salts with compounds of formula (I) there may be mentioned by way of non-limiting example hydrochloric, sulphuric, tartaric, maleic, fumaric, oxalic, methanesulphonic and camphoric acids etc.

Preferred compounds of the invention are those in which $R_3$ represents a group of formula (G) in which p is other than 0, $R_5$ represents a group of formula (G) in which n and p are other than 0, $R_3$ and $R_4$ together with the aromatic ring carrying them form a benzofuran system.

The present invention also extends to processes for the preparation of compounds of formula (I), which are characterised as follows:

either (PROCESS A) a compound of formula (II)

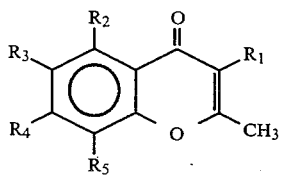

(II)

in which $R_1$, $R_2$, $R_3$, $R_4$ and $R_5$ have the same meaning as in formula (I), is condensed, in the presence of a basic agent in a polar solvent, by heating at the reflux point of the solvent with a substituted benzaldehyde (III)

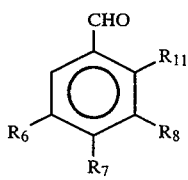

(III)

in which $R_6$, $R_7$, $R_8$ *l and* $R_{11}$ have the same meaning as in formula (I), to yield, after cooling and filtration of the reaction mixture, a compound of formula (I);

or (PROCESS B) two molecules of triphenylalkylphosphonium (or triphenylalkoxymethylphosphonium) halide of formula (IV):

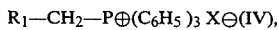

$R_1$—$CH_2$—$P\oplus(C_6H_5)_3$ $X\ominus$ (IV), in which $R_1$ represents a hydrogen atom, a lower alkyl group or a lower alkoxy group and $X\ominus$ represents the anion of a hydracid, which are suspended in an organic solvent, preferably anhydrous tetrahydrofuran, are treated with a strong base, preferably a solution of n-butyllithium in hexane, which is added progressively and with stirring, the solution obtained after several hours' contact, preferably at room temperature, in turn being treated under an inert atmosphere with a molecule of alkyl 2-hydroxybenzoate of formula (V):

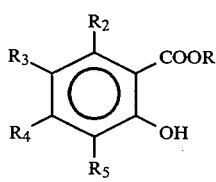

(V)

in which $R_2$, $R_3$, $R_4$ and $R_5$ have the same meaning as in formula (I) and R represents a lower alkyl group, dissolved in the solvent chosen above, the resulting mixture then being heated to a temperature preferably of from 50° C. to 60° C. to yield, after filtration of the reaction mixture and removal in vacuo of the solvents, a compound of formula (VI):

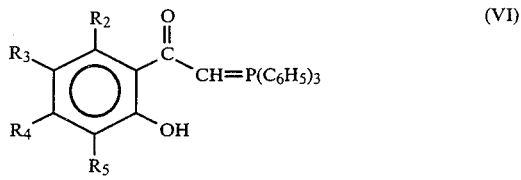

(VI)

in which $R_2$, $R_3$, $R_4$ and $R_5$ are as defined above, to which compound, placed in anhydrous pyridine and under an inert atmosphere, there is added cinnamic acid chloride of formula (VII):

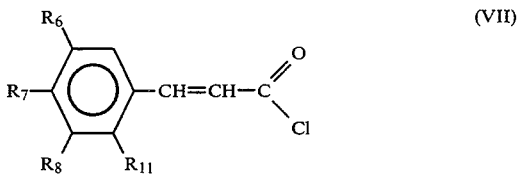

(VII)

in which $R_6$, $R_7$, $R_8$ and $R_{11}$ have the same meaning as in formula (I), and the mixture is heated at a temperature preferably of 60° C. for approximately one day to yield, after removal of the solvent, taking up in an appropriate organic solvent and successive extractions in alkaline medium and, finally, removal of the solvents, a compound of formula (I) which, whichever process has been used to obtain it, is, if desired, either, when $R_1$, $R_2$, $R_3$, $R_4$, $R_5$, $R_6$, $R_7$, $R_8$ and $R_{11}$ represent (or comprise) a carboxyl group, converted into a salt with a pharmaceutically acceptable base or esterified with a pharmaceutically acceptable alcohol or, when the same radicals comprise a basic group, converted into a salt with a pharmaceutically acceptable acid, or separated into its stereoisomers, diastereoisomers or enantiomers by a method of crystallisation or chromatography, and then, if desired, when $R_2$, $R_3$, $R_4$, $R_5$, $R_6$, $R_7$, $R_8$ or $R_{11}$ represent (or comprise) a carboxy group, is subjected to the same operations as those described above.

Process A is preferentially used to obtain:
2-styryl-5H-furo[3,2-g]1-benzopyran-5-ones (IX) from compounds (VIII):

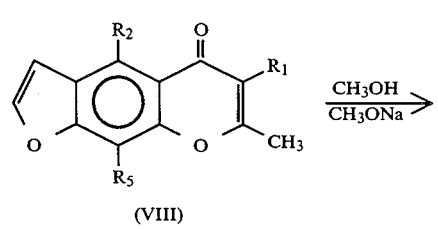

(VIII)

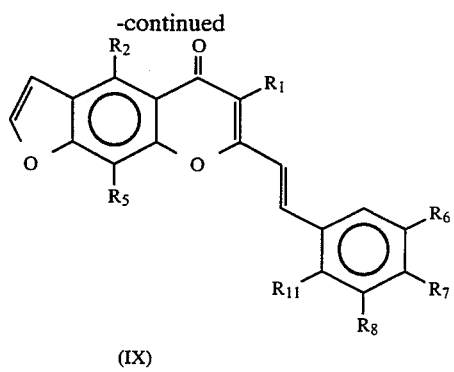

(IX)

the yields varying from 65 to 70%, and alkyl (2-styryl-4-oxo-4H-1-benzopyran-6-yl)-carboxylates (XI) from compounds (X):

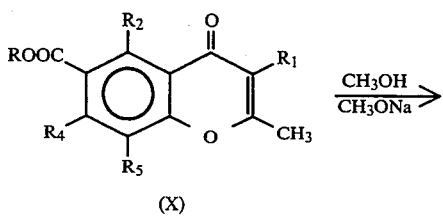

(X)

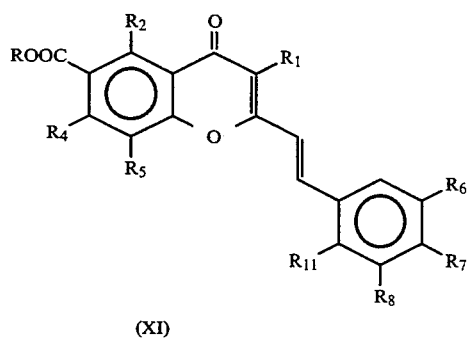

(XI)

in which R represents a hydrogen atom or a lower alkyl group.

The compounds of formula (I) have valuable pharmacological properties. They inhibit the growth of the L1210 cell line to a greater extent than does retinoic acid and, of particular value for therapeutic use, induce cell differentiation of the HL60 cell line without, like the reference compound retinoic acid, causing hypervitamin A toxicity. In vivo in mice, certain compounds prove active against C38 adenocarcinoma.

The compounds described in the present invention are therefore used therapeutically as anti-tumour agents for the treatment or prophylaxis of benign or malignant neoplasms, including carcinoma of the colon, as well as for conventional indications of that therapeutic class, such as skin disorders (acne, psoriasis) and also degenerative disorders and/or inflammatory disorders of the mucosa.

The present invention also relates to pharmaceutical compositions containing products of formula (I), or an addition salt thereof with a pharmaceutically acceptable acid or base when the radicals $R_1$ to $R_8$ represent a salt-forming group, alone or in combination with one or more pharmaceutically acceptable, non-toxic inert vehicles or excipients.

Of the pharmaceutical compositions according to the invention there shall be mentioned more especially those suitable for oral, parenteral, nasal, rectal, perlingual, ocular or respiratory administration, and especially simple or dragéed tablets, sublingual tablets, sachets, cachets, gelatin capsules, glossettes, tablets, suppositories, creams, ointments, skin gels, injectable or drinkable preparations, aerosols, eye or nose drops, etc.

The posology varies according to the age and weight of the patient, the method of administration, and the nature of the therapeutic indication and of possible associated treatments, and ranges from 0.1 to 200 mg per day.

The following Examples illustrate the invention but do not limit it in any way.

The infra-red spectra are carried out either as a film or as a (1%) potassium bromide disc, depending on whether the products are liquid or solid. The nuclear magnetic resonance spectra, unless indicated otherwise, are carried out in deuterium chloroform or in hexadeuterium dimethyl sulphoxide with a 100 MHz apparatus using tetramethylsilane as internal reference, the displacements being expressed in ppm.

The Preparations do not form part of the invention but illustrate methods of carrying it out.

PREPARATION 1

4-METHOXY-7-STYRYL-5H-FURO[3,2-g]-BENZO-PYRAN-5-ONE

A solution of sodium methoxide (34.8 mmol; 0.80 g of Na in 20 ml of methanol) and then 1.32 ml (13.05 mmol) of benzaldehyde are added, with stirring and with protection from moisture, to 2 g (8.7 mmol) of visnagin dissolved with the application of heat in the minimum amount of anhydrous methanol (150 ml). After having been refluxed for 24 hours, the reaction mixture is filtered and the precipitate is extracted several times with diethyl ether and then dried; 1.6 g of beige crystals are obtained.

Yield 56 % M.p.: 169° C. (diethyl ether) Elemental analysis: Calculated: C=75.46%, H=4.43%; Found C=74.61%, H=4.81%.

IR (1% KBr, cm$^{-1}$) 2820, 1650, 1615, 1460, 1150

$^1$H NMR (CDCl$_3$, δ ppm): 4.20 (s, 3H, OCH$_3$ (4-)); 6.20 (s, 1H, H6); 6.65–6.80 (d, J$_{α-β}$=16 Hz, 1H, H$_α$); 7.05–7.60 (m, 9H, H2, H4, H-ar and H$_β$)

MS (m/z): 318, 289, 215, 190, 161, 128

EXAMPLE 1

Methyl 5,7-Dimethoxy-4-Oxo-2-Styryl-4H-1-Benzopyran-6-Carboxylate

STAGE A

Methyl 7-Hydroxy-5-Methoxy-2-Methyl-4-Oxo-4H 1-Benzopyran-6-Carboxylate 2.6 g (53 mmol) of sodium cyanide and then 18.50 g (223 mmol, 25 eq.) of activated manganese dioxide are added to 2 g (8.5 mmol) of 6-formyl-7-hydroxy-5-methoxy-2-methyl-4H -benzopyran-4-one (A. SCHONBERG, N. BADRAN and N. A. STARKONSKY, J. Am. Chem. Soc., 1953, 75, 4992) suspended in 105 ml of methanol acidified with 2.6 ml of acetic acid. After having been stirred for 4 hours at room temperature, the reaction mixture, diluted with 200 ml of ethyl acetate, is filtered to remove insoluble material (excess MnO$_2$) and the solvents are evaporated. The powdery residue is taken up in water and filtered. 1.80 g of a beige powder are obtained.

Yield: 80% M.p.: 200° C.

STAGE B

Methyl 5,7-Dimethoxy-2-Methyl-4-Oxo-4H-1-Benzopyran-6-Carboxylate

With protection from moisture, 0.304 g (7.6 mmol) of sodium hydride (60% dispersion) is slowly added at 60° C., with stirring, to 2 g (7.6 mmol) of methyl 7-hydroxy-5-methoxy-2-methyl-4-oxo-4H-1-benzopyran-6-carboxylate dissolved in 25 ml of anhydrous DMF. After a contact period of 1½ hours, 0.95 ml (15.2 mmol) of iodomethane is added to the reaction mixture and stirring is continued for 2 hours. After decomposition of excess sodium hydride by the addition of 6 ml of methanol, the reaction mixture is diluted with diethyl ether and then poured onto 100 ml of water. The precipitate formed is filtered and then washed several times with diethyl ether. Purification of the powdery residue by chromatography on a silica gel column (eluant: $CH_2Cl_2/CH_3OH$: 99/1) yields 2.0 g of white crystals.

Yield: 95% M.p.: 188° C. Elemental analysis: $C_{14}H_{14}O_6$, 0.5 $H_2O$ MW: 287.27 Calculated: C=58.53%, H=5.26%; Found: C=58.53%, H=5.22%.

STAGE C

Methyl 5,7-Dimethoxy-4-Oxo-2-Styryl-4H-1Benzopyran-6-Carboxylate

A solution of sodium methoxide (28.8 mmol, 0.662 g of Na in 20 ml of $CH_3OH$) and then 1.15 g (10.8 mmol) of benzaldehyde are added, with stirring and with protection from moisture, to 2 g (7.2 mmol) of methyl 5,7-dimethoxy-2-methyl-4-oxo-4H-1-benzopyran-6-carboxylate dissolved with the application of heat in 250 ml of anhydrous methanol. After having been refluxed for 24 hours, the reaction mixture is concentrated (removal of approximately 200 ml of methanol), then cooled. The precipitate is filtered and extracted several times with diethyl ether; 2.2 g of white crystals are obtained.

Yield: 80% M.p.: 172° C. (diethyl ether) Elemental analysis: $C_{21}H_{18}O_6$, MW: 366.37 Calculated C=68.84%, H=4.95%; Found: C=68.97%, H=5.31%.

IR (1% KBr, $cm^{-1}$) 1735, 1645, 1610, 1590, 750 and 690

$^1$H NMR (CDCl3, δ ppm) 3.85 (s, 3H, COOCH3); 3.90 (s, 3H, OCH3 (7-)); 3.95 (s, 3H, OCH3 (5-)); 6.20 (s, 1H, H3); 6.70 (d, Jα-β=16 Hz, 1H, CH=CH—C6H5); 7.50 (d, Jβ-α=16 Hz, 1H, CH=CH-C6H5); 7.40–7.60 (m, 6H, H-ar)

MS (m/z): 366, 351, 334, 305, 277, 128

EXAMPLE 2

Methyl 5,7-Dimethoxy-4-Oxo-2-(3,4-Dimethoxy-Styryl)-4H-1-Benzopyran-6-Carboxylate Prepared in accordance with the protocol described for Stage C of Example 1.

Yield: 81% M.p.: 176° C. (diethyl ether) Elemental analysis: C23H22O8, 0.5 H2O; MW: 435.42 Calculated: C=63.44%, H=5.32%; Found: C=63.42%, H=5.39%.

IR (1% KBr, $cm^{-1}$) 1730, 1640, 1620, 1600, 840 and 800

1H NMR (CDCl3, δ ppm) 3.80 (s, 3H, OCH3 (3'-)); 3.85 (s, 3H, COOCH3); 3.90 (s, 6H, OCH3 (7- and 4'-)); 3.95 (s, 3H, OCH3 (5-)); 6.15 (s, 1H, H3); 6.50 (d, Jα-β=16 Hz, 1H, CH=CH-Ar); 6.75–6.90 (m, 4H, H-ar); 7.05 (d, Jβ-α=16 Hz, 1H, CH=CH-Ar);

MS (m/z) 426, 411, 394, 365, 337, 188

EXAMPLE 3

Methyl 5,7-Dimethoxy-4-Oxo-2-(3,4,5-Tri-Methoxystyryl)-4H-1-Benzopyran-6-Carboxylate Prepared in accordance with the protocol described for Stage C of Example 1 (except for the heating time: 36 hours refluxing with methanol).

Yield: 65% M.p.: 171° C. (diethyl ether) Elemental analysis: $C_{24}H_{24}O_9$, 1 $H_2O$; MW: 474.45 Calculated: C=60.75%, H=5.22%; Found: C=60.26%, H=5.58%.

IR (1% KBr, $cm^{-1}$) 1735, 1640, 1610, 1575 and 850

$^1$H NMR (CDCl3, δppm) 3.80 (s, 6H, OCH3 (3'- and 5'-)); 3.85 (s, 3H, COOCH3); 3.90 (s, 6H, OCH3 (7- and 4'-)); 3.95 (s, 3H, OCH3 (5-)); 6.20 (s, 1H, H3); 6.60 (d, Jα-β=16 Hz, 1H, CH=CH-Ar); 6.70–6.80 (m, 3H); 7.40 (d, Jβ-α=16 Hz, 1H, CH=CH-Ar).

MS (m/z): 456, 441, 424, 395, 367, 218.

EXAMPLE 4

Methyl 5,7-Dimethoxy-2-(4-Methoxycarbonyl-Styryl)-4H-1-Benzopyran-6-Carboxylate Prepared in accordance with the protocol described for Stage C of Example 1 (except for the heating time: 3 hours refluxing with methanol).

Yield: 70% M.p.: 197@C (diethyl ether) Elemental analysis: $C_{23}H_{20}O_8$, MW: 424.40 Calculated: C=65.09%, H=4.79%; Found: C=64.93%, H=4.94%.

IR (1% KBr, $cm^{-1}$) 1735, 1720, 1640, 1610, 1600, 780

$^1$H NMR (CDCl3, δ ppm) 3.85 (s, 3H, COOCH3 (6-)); 3.90 (s, 6H, OCH3 (7-) and COOCH3 (4'-)); 3.95 (s, 3H, OCH3 (5-)); 6.20 (s, 1H, H3); 6.75 (d, Jα-β=16 Hz, 1H, CH=CH-Ar); 6.80 (s, 1H, H8); 7.60 (d, Jβ-α=16 Hz, 1H, CH=CH-Ar); 7.60–8.10 (m, 4H, H-ar)

MS (m/z): 424, 409, 392, 363, 335

EXAMPLE 5

4-[(5,7-Dimethoxy-6-Methoxycarbonyl-4-Oxo-4H-1-Benzopyran-2-yl)-Vin-1-yl]-Benzoic Acid Prepared in accordance with the protocol described for Stage C of Example 1.

Yield: 55% M.p.: 244° C. (ethanol) Elemental analysis: $C_{22}H_{18}O_8$, 1 $H_2O$; MW: 428.39 Calculated: C=60.75%, H=5.52%; Found: C=61.12%, H=5.45%.

IR (1% KBr, $cm^{-1}$) 1735, 1700, 1640, 1610, 1580, 800

$^1$H NMR (CDCl3, δ ppm) 3.85 (s, 3H, COOCH3 (6-)); 3.90 (s, 3H, OCH3 (7-)); 3.95 (s, 3H, OCH3 (5-)); 6.35 (s, 1H, H3); 7.30 (d, Jα-β=17 Hz, 1H, CH=CH-Ar); 7.75–8.05 (m, 5H, H-ar); 8.00 (d, Jβ-α=17 Hz, 1H, CH=CH-Ar); 13.00 (s, 1H, COOH)

EXAMPLE 6

Methyl 4-Oxo-2-Styryl-5,7,8-Trimethoxy-4H-1-Benzopyran-6-Carboxylate

STAGE A

Methyl 5,7-Dimethoxy-7-Hydroxy-2-Methyl-4-Oxo-4H-1-Benzopyran-6-Carboxylate 1.84 g (37.5 mmol) of sodium cyanide and then 13.04 g (161 mmol) of activated manganese dioxide are added to 2 g (7.5 mmol) of 5,8-dimethoxy-6-formyl-7-hydroxy-2-methyl-4H-1-benzopyran-4-one (R. B. GAMMILL and S. A. NASH, J. Org. Chem., 1986, 51, 3116) suspended in 75 ml of methanol acidified with 2 ml of acetic acid. After having been stirred for 4 hours at room temperature, the reaction mixture, diluted with 100 ml of ethyl acetate, is filtered to remove insoluble material (excess $MnO_2$) and the solvents are evaporated. The powdery residue is taken up in $H_2O$ and filtered. 1.103 g of a greyish powder are obtained.

Yield: 50% M.p.: 210° C.

STAGE B

Methyl 2-Methyl-4-Oxo-5,7,8-Trimethoxy-4H-1-Benzopyran-6-Carboxylate

With protection from moisture, 0.42 g (10.6 mmol) of sodium hydride (60% dispersion) is slowly added at 60° C., with stirring, to 3.10 g (10.6 mmol) of methyl 5,8-dimethoxy-7-hydroxy-2-methyl-4-oxo-4H-1-benzopyran-6-carboxylate dissolved in 50 ml of anhydrous dimethylformamide. After a contact period of 1½ hours, 1.30 ml (21.2 mmol) of iodomethane are added to the reaction mixture and stirring is continued for 2 hours. After decomposition of the excess sodium hydride by the addition of methanol, the reaction mixture, diluted with diethyl ether, is filtered. Evaporation of the filtrate results in an orange oil which is taken up in water and extracted 3 times with 50 ml of diethyl ether each time. The combined organic phases are washed with a saturated solution of NaCl and dried over $Na_2SO_4$ and then the solvents are removed. Chromatography of the powdery residue on a silica gel column (70–230 mesh; eluant: $CH_2Cl_2/CH_3OH$: 99/1) yields 2.5 g of orange crystals.

Yield: 76% M.p.: 125° C.

STAGE C

Methyl 4-Oxo-2-Styryl-5,7,8-Trimethoxy-4H-1-Benzopyran-6-Carboxylate

A solution of sodium methoxide (6.48 mmol; 0.15 g of Na in 10 ml of anhydrous methanol) and then 0.52 g (4.85 mmol) of benzaldehyde are added, with stirring and with protection from moisture, to 1 g (3.24 mmol) of methyl 2-methyl-4-oxo-5,7,8-trimethoxy-4H-1-benzopyran-6-carboxylate dissolved with the application of heat in 200 ml of anhydrous methanol. After having been refluxed for 24 hours, the reaction mixture is concentrated; the residue, taken up in 150 ml of water, is acidified with a N HCl solution and extracted three times with 50 ml of diethyl ether each time. Removal of the solvents yields an orange oil which, after purification by chromatography on a silica gel column (70–230 mesh; eluant: diisopropyl ether), yields 0.250 g of orange crystals.

Yield: 40% M.p.: 164° C. Elemental analysis: $C_{22}H_{20}O_7$, 1 $H_2O$, MW: 414.39 Calculated C=63.76%, H=5.35%; Found C=63.23%, H=5.65%.

IR (1% KBr, $cm^{-1}$) 1740, 1635, 1620, 1600, 750 and 690

$^1$H NMR ($CDCl_3$, δ ppm) 3.75 (s, 3H, $OCH_3$ (8-)); 3.85 (s, 3H, $COOCH_3$ (6-)); 3.90 (s, 3H, $OCH_3$ (7-)); 4.00 (s, 3H, $OCH_3$ (5-)); 6.75 (s, 1H H3); 7.40–7.55 (m, 6H, H-ar and H-vinyl); 8.00 (d, Jβ-α=17 Hz, 1H, CH=CH-$C_6H_5$)

EXAMPLE 7

4-Methoxy-7-(3,4-Dimethoxystyryl)-5H-Furo[3,2-g]Benzopyran-5-One

Prepared in accordance with the protocol described for Preparation 1.

Yield: 84% M.p.: 182° C. (diethyl ether) Elemental analysis: $C_{22}H_{18}O_6$, MW=396.38 Calculated: C=66.66%, H=5.08%; Found: C=66.49%, H=4.84%.

IR (1% KBr, $cm^{-1}$) 2820, 1645, 1620, 1590, 850 and 820.

$^1$H NMR ($CDCl_3$, δ ppm) 3.90 and 3.95 (s, 6H, $OCH_3$ (3'- and 4'-)); 4.20 (s, 3H, $OCH_3$ (4-)); 6.15 (s, 1H, H6); 6.55 (d, Jα-β=16 Hz, 1H, CH=CH-Ar); 6.90–7.40 (m, 6H H-vinyl, H-ar, H3 and 9); 7.60 (d, $J_{H2-H3}$=2 Hz, 1H, H3)

MS (m/z): 378, 349, 215, 190, 188, 161

EXAMPLE 8

4-Methoxy-7-(3,4,5-Trimethoxystyryl)-5H-Furo[3,2-g]Benzopyran-5-One

Prepared in accordance with the protocol described for Preparation 1, with the exception of the heating time which is reduced to 30 minutes.

Yield: 70% M.p.: 204° C. (diethyl ether) Elemental analysis: $C_{23}H_{20}O_7$, MW=408.41 Calculated: C=67.66%, H=4.93%; Found: C=67.50%, H=5.04%.

IR (1% KBr, $cm^{-1}$) 2820, 1645, 1620, 1580, 840

$^1$H NMR ($CDCl_3$, δ ppm) 3.90 and 3.95 (s, 9H, $OCH_3$ (3'-, 4'-, 5-',)); 4.20 (s, 3H, $OCH_3$ (4-)); 6.20 (s, 1H, H6); 6.65 (d, Jα-β=16 Hz, 1H, Hα); 6.55–6.80 (m, 2H, H2' and 6'); 7.05 (d, $J_{H3-H2}$=2 Hz, 1H, H3); 7.40 (s, 1H, H9); 7.50 (d, Jβ-α=16 Hz, 1H, Hβ); 7.60 (d, $J_{H2-H3}$=2 Hz, 1H, H2)

MS (m/z) 408, 379, 218, 190, 161

EXAMPLE 9

Methyl 4-(2-(4-Methoxy-5-Oxo-5H-Furo-[3,2-g]Benzopyran-7-yl)-Vin-1-yl)-Benzoate Prepared in accordance with the protocol described for Preparation 1, with the exception of the heating time which is reduced to 30 minutes.

Yield: 98% M.p.: 198° C. (diethyl ether) Elemental analysis: $C_{22}H_{16}O_6$, MW=376.37 Calculated: C=70.21%, H=4.28%; Found: C=69.62%, H=4.57%.

IR (1% KBr, $cm^{-1}$) 1730, 1650, 1610, 1580, 770.

$^1$H NMR ($CDCl_3$, ppm) 3.95 (S, 3H, $COOCH_3$); 4.20 (s, 3H, $OCH_3$); 6.25 (s, 1H, H6); 6.80 (d, Jα-β=16 Hz, 1H, Hα); 7.05 (d, $J_{H3-H2}$=2 Hz, 1H, H3); 7.40 (d, Jβ-α=16 Hz, 1H, Hβ); 7.35–7.65 (m, 2H, H2 and H9); 7.60–8.10 (m, 4H, H2', 3', 5' and 6').

MS (m/z): 376, 347, 215, 161

PREPARATION 2

4,9-Dimethoxy-7-Styryl-5H-Furo[3,2-g]Benzopyran-5-One

A solution of sodium ethoxide (230 mg of Na in 10 ml of ethanol) is added dropwise to a clear solution of 2.60 g (10 mmol) of khellin (dissolved with the application of heat) and 1.060 g (10 mmol) of benzaldehyde. After 30 minutes at room temperature, the product precipitates in the reaction mixture. Stirring is continued for 12 hours. The crystals are subsequently filtered and then washed with ethanol.

Yield: 72% M.P._Kofler_: 192° C. (diethyl ether) Elemental analysis: $C_{21}H_{16}O_5$, MW=348.36 Calculated: C=72.40%, H=4.63%; Found: C=71.98%, H=4.91%.

IR (1% KBr, cm$^{-1}$) 1640, 1615, 1590, 750, 690.

$^1$H NMR (CDCl$_3$, δ ppm) 4.10 (s, 3H, OCH$_3$ (9-)); 4.25 (s, 3H, OCH$_3$ (4-)); 6.20 (s, 1H, H6); 6.75 (d, Jα-β=16 Hz, 1H, Hα); 7.00 (d, $J_{H3-H2}$=2 Hz, 1H, H3 ); 7.25–7.70 (m, 6H, Hβ and H-ar); 7.65 (d, $J_{H2-H3}$=2 Hz, 1H, H2).

EXAMPLE 10

(2-Styrylchromon-8-Yl)-Acetic Acid

STAGE A

2,8-Dimethylchromone 19 ml (0.17 mol) of acetic anhydride and 17 ml (0.21 mol) of pyridine are added to 40 g (0.097 mol) of (2-hydroxy-3-methylbenzoyl)-methylenetriphenylphosphorane dissolved in 250 ml of anhydrous toluene. The reaction mixture is heated at reflux for 5 hours and then, after having been cooled, filtered to remove the pyridinium salt that has formed. The filtrate is washed with a 15% aqueous sodium carbonate solution and the solvents are removed in vacuo. Chromatography of the powdery residue on a silica gel column (70–230 mesh; eluant: CH$_2$Cl$_2$/CH$_3$OH: 99/1) yields 9.5 g of white crystals.

Yield: 56% M.p.: 114° C. Elemental analysis: $C_{11}H_{10}O_2$, MW=174.20

IR (1% KBr, cm$^{-1}$) 1640, 1600.

$^1$H NMR (CDCl$_3$, δ ppm) 2.40 (s, 3H, CH$_3$ (8-)); 2.50 (s, 3H, CH$_3$ (2-)); 6.20 (s, 1H, H3); 7.25 (t, $J_{6-5}$=$J_{6-7}$=8.0 Hz, 1H, H6); 7.50 (dd, $J_{7-6}$ and $J_{7-5}$=2 Hz, 1H, H7); 8.00 (dd, $J_{5-6}$=8.00 Hz and $J_{5-7}$=2 Hz, 1H, H5 ).

STAGE B

8-Bromoethyl-2-Methylchromone

A solution of 3 g (17 mmol) of 2,8-dimethylchromone in 50 ml of carbon tetrachloride, to which 1.5 mg of benzoyl peroxide and 3.0 g (17 mmol) of N-bromosuccinimide have been added, is heated at reflux for 6 hours with stirring and with UV irradiation (Philips 500 W lamp). The cooled reaction mixture is filtered to remove supernatant succinimide and the solvent is evaporated. Recrystallisation of the powder from cyclohexane yields 3.45 g of crystals.

Yield: 80% M.p.: 100° C. Elemental analysis: $C_{11}H_9O_2Br$, MW=253.10

IR (1% KBr, cm$^{-1}$) 1640, 1600, 750.

$^1$H NMR (CDCl$_3$, δ ppm) 2.45 (s, 3H, CH$_3$ (2-)); 4.70 (s, 2H, CH$_2$-Br); 6.20 (s, 1H, H3); 7.30 (t, 1H, $J_{6-5}$=$J_{6-7}$=7 Hz, H6); 7.95 (dd, $J_{7-6}$ and $J_{7-5}$=2 Hz, 1H, H7); 8.20 (dd, 1H, $J_{5-6}$=7 Hz and $J_{5-7}$=2 Hz, H5).

STAGE C

8-Cyanomethyl-2-Methylchromone 5.45 g (35 mmol) of tetraethylammonium cyanide are added to 5.9 g (23 mmol) of 8-bromomethyl-2-methylchromone dissolved in 200 ml of anhydrous dichloromethane. After contact for one night at room temperature, the solvent is evaporated in vacuo and the residue is taken up in diethyl ether and then filtered. Evaporation of the filtrate and purification by chromatography on a silica gel column (70–230 mesh; eluant: CH$_2$Cl$_2$) yield 2.40 g of white crystals.

Yield: 52% M.p.: 138° C. Elemental analysis: $C_{12}H_9O_2N$, MW=199.21

IR (1% KBr, cm$^{-1}$) 2220, 1650, 1600.

$^1$H NMR (CDCl$_3$, δ ppm) 2.45 (s, 3H, CH$_3$ (2-)); 3.95 (s, 2H, CH$_2$—CN); 6.20 (s, 1H, H3); 7.50 (t, $J_{6-5}$=$J_{6-7}$=9 Hz, 1H, H6); 7.80 (dd, $J_{7-6}$ and $J_{7-5}$=2 Hz, 1H, H7); 8.20 (dd, $J_{5-6}$=9 Hz and $J_{5-7}$=2 Hz, 1H, H5).

STAGE D

(2-Methylchromon-8-Yl)-Acetic Acid 4 ml of concentrated sulphuric acid are added dropwise to a solution of 0.70 g (3.5 mmol) of 8-cyanomethyl-2-methylchromone in 8 ml of 50% aqueous acetic acid (v/v). When the addition is complete, the reaction mixture is heated at reflux for 7 hours. The cooled reaction mixture is poured onto 250 ml of iced water and placed in a refrigerator for one night. The precipitate formed is dissolved in a 5% sodium hydrogen carbonate solution, which has been heated beforehand to a temperature of between 50° and 60° C., and is then filtered. After acidification of the filtrate with concentrated HCl, the insoluble material obtained is separated by filtration and then washed 3 times with 20 ml of water each time and dried (0.73 g of whitish crystals).

Yield: 96% M.p.: 228° C. Elemental analysis: $C_{12}H_{10}O_4$, MW =218.21

IR (1% KBr, cm$^{-1}$) 3400–3200, 1700, 1640.

$^1$H NMR (DMSO-d$_6$, δ ppm): 2.35 (s, 3H, CH$_3$ (2-)); 3.90 (s, 2H, CH$_2$—COOH); 6.25 (s, 1H, H3); 7.40 (t, $J_{6-5}$=9 Hz and $J_{6-7}$=9 Hz, 1H, H6); 7.60 (dd, $J_{7-6}$ and $J_{7-5}$ = 2 Hz, 1H, H7); 8.00 (dd, $J_{5-6}$=9 Hz and $J_{5-7}$=2 Hz, 1H, H5); 12.50 (s, 1H, OH).

STAGE E

(2-Styrylmethylchromon-8-Yl)-Acetic Acid

A solution of sodium methoxide (6.7 mmol; 0.155 g of Na in 20 ml of CH$_3$OH) and then 0.35 ml (3.4 mmol) of benzaldehyde are added, with stirring and with protection from moisture, to 0.73 g (3.34 mmol) of (2-methylchromon-8-yl)-acetic acid dissolved with the application of heat in the minimum amount of anhydrous methanol. After having been refluxed for 24 hours, the reaction mixture is evaporated and the residue is dissolved in a 5% aqueous sodium hydrogen carbonate solution that has been heated beforehand to a temperature of between 50° and 60° C. (the solution being filtered if necessary). After acidification of the filtrate with N HCl, the insoluble material is removed by filtration and then washed 3 times with 20 ml of water each time and finally dried. Washing the resulting yellow powder in chloroform that has been heated beforehand to 30°–40° C. yields 0.70 g of beige crystals.

Yield: 55% M.p.: 202° C. Elemental analysis: $C_{19}H_{14}O_4$, MW=315.31 Calculated: C=72.37%, H=4.79%; Found: C=72.40%, H =4.80%.

IR (1% KBr, cm$^{-1}$) 3200–2900, 1710, 1600 and 1570

$^1$H NMR (DMSO-d$_6$, δ ppm) 4.00 (s, 2H, CH$_2$—COOH); 6.45 (s, 1H, H3); 7.30–8.00 (m, 10H, H-ar and H-vinyl); 11.50 (s, 1H, OH)

$^{13}$Hc NMR (DMSO-d$_6$, δ ppm): 177 (C4); 172 (C10); 161 (C8a); 154 (C2); 136.5 (C7); 136 (C1′); 135 (Cβ); 130 (C5a); 129 (C4′); 128 (C3′ 5′); 126 (C2′-6′); 124.9 (C5); 123.7 (C8); 123.5 (C6); 121 (Cα); 110 (C3); 37 (C9).

EXAMPLE 11

(2-(3′,4′,5′-Trimethoxystyryl)-chromon -8-Yl)-Acetic Acid

Prepared in accordance with the protocol described in Stage E of Example 10. Orange crystals.

Yield: 62% M.p.: 212° C. Elemental analysis: $C_{22}H_{20}O_7$, H$_2$O MW=414.40 Calculated: C=63.76%, S=5.35%; Found: C=63.95%, H=5.30%.

IR (1% KBr, cm$^{-1}$) 3200–2500, 2820, 1710, 1620, 1600 and 1580.

$^1$H NMR (CDCl$_3$, δ ppm) 3.70 (s, 3H, OCH3 (4′-)); 3.80 (s, 6H, OCH$_3$ (3′- and 5′-)); 4.00 (s, 2H, CH$_2$—COOH); 6.40 (s, 1H, H3); 7.00–7.70 (m, 7S, H-ar, H-vinyl and H2′, 6′); 12.50 (s.e., 1H, OH)

$^{13}$C NMR (DMSO-d$_6$, δ ppm): 177(C4); 173 (C10); 162 (C8a); 154 (C2); 142 (C4′); 140 (C7); 136 (C1′); 135 (Cβ); 132 (C5a); 131 (C3′- 5′); 128 (C8); 127 (C2′-6′); 124 (C5); 122 (C6); 119 (Cα); 110 (C3); 61 (OCH$_3$ (4′-)); 57 (OCH$_3$ (3′- and 5′-)); 39 (C9).

EXAMPLE 12

(2-(4-Carboxystyryl)-chromon-8-Yl)-Acetic Acid

Prepared in accordance with the protocol described in Example 10. Yellow crystals.

Yield: 70% M.p.: >305° C. Elemental analysis: $C_{20}H_{14}O_6$, 0.5 H$_2$O MW=359.32 Theory: C=66.85%, H=4.21%; Found: C=66.98%, H=4.15%.

IR (1% KBr, cm$^{-1}$) 3200–2500, 1730 and 1710, 1620, 1600 and 1570.

$^1$H NMR (CDCl$_3$, δ ppm) 4.00 (s, 2H, CH2COOH); 6.50 (s, 1H, H3); 7.20–8.00 (m, 10H, H-ar, H-vinyl and H2′, 3′, 5′, 6′, OH); 13.00 (s., 1H, OH)

$^{13}$C NMR (DMSO-d$_6$, δ ppm) 177(C4); 172 (C10); 168 (C11); 160 (C8a); 154 (C2); 138 (C4); 136 (C7); 135.5 (C1′); 135 (Cβ); 131 (C5a); 129.5 (C3′-5′); 127 (C2′-6′); 125 (C5); 124 (C8); 123 (C6); 122 (Cα); 112 (C3); 39 (C9).

EXAMPLE 13

(3-Methyl-4-Oxo-2-Styryl-4H-1-Benzopyran-8-Yl)-Acetic Acid

STAGE A 2,3-Dimethyl-7-Methoxy-4H-1-Benzopyran-4-One 11.9 g (66.11 mmol) of 2-hydroxy-4-methoxypropiophenone in 24 ml of acetic anhydride are heated at reflux for 7 hours in the presence of 14.90 g (181.56 mmol) of freshly melted sodium acetate. After excess acetic anhydride has been removed in vacuo, the reaction mixture is poured onto 200 ml of water and extracted 3 times with 50 ml of dichloromethane each time. The combined organic phases are washed with a saturated solution of sodium chloride and then dried over sodium sulphate. Evaporation of the solvents and purification by chromatography on a silica gel column (eluant: CH$_2$Cl$_2$) yield 7.45 g of beige crystals.

Yield: 55% M.p.: 117° C. Elemental analysis: $C_{12}H_{12}O_3$, MW=204.22

IR (1% KBr, cm$^{-1}$) 2820, 1630, 1600–1580, 1440.

$^1$H NMR (CDCl$_3$, δ ppm) 2.00 (s, 3H, CH3 (3-)); 2.40 (s, 3H, CH$_3$ (2-)); 3.90 (s, 3H, OCH$_3$ (7-)); 6.80 (d, J8-6 =2 Hz, 1H, H8); 6.90 (dd, J$_{6-5}$=9 Hz and J$_{6-8}$=2 Hz, 1H, H6); 8.10 (d, J$_{5-6}$=9 Hz, 1H, H5).

STAGE B

8-Chloromethyl-2,3-Dimethyl-7-Methoxy-4H-1-Benzopyran-4-One 4.9 g (23.48 mmol) of 2,3-dimethyl-7-methoxy-4H-1-benzopyran-4-one are heated at 60° C. for 5 hours, with stirring, in a mixture of 35 ml of conc. hydrochloric acid and 1.2 g (40 mmol) of polyoxymethylene. After having been cooled, the reaction mixture is poured onto 100 ml of iced water and left for one night at 5° C. After filtration of the reaction mixture, the precipitate recovered is washed 3 times with 50 ml of water each time and then dried. 5.15 g of white crystals are obtained.

Yield: 87% M.p.$_{Kofler}$: 171° C. Elemental analysis: $C_{13}H_{13}O_3Cl$ MW=253.60

IR (1% KBr, cm$^{-1}$) 2820, 1640, 1600–1590, 1440, 790.

$^1$H NMR (CDCl$_3$, δ ppm) 2.05 (s, 3H, CH3 (3-)); 2.45 (s, 3H, CH$_3$ (2-)); 4.00 (s, 3H, OCH$_3$); 4.90 (s, 2H, CH$_2$Cl); 7.00 (d, J$_{6-5}$=9 Hz, 1H, H6 ); 8.20 (d, J$_{5-6}$=9 Hz, 1H, H5).

STAGE C (2,3-Dimethyl-7-Methoxy-4-Oxo-4H-1-Benzopyran-8-Yl)-Acetonitrile

A suspension of 3.27 g (12.96 mmol) of 8-chloromethyl-2,3-dimethyl-7-methoxy-4H-1-benzopyran-4-one in 38 ml of boiling ethanol is added dropwise, with stirring, to a solution, heated beforehand to a temperature of between 60° and 70° C., of 1.47 g (22.53 mmol) of potassium cyanide in 8 ml of water. When the addition is complete, the reaction mixture is heated at reflux for 4 hours at 70° C. After cooling the reaction mixture, adding iced water and filtering, the resulting crystals are dried and purified by chromatography on a silica gel column (eluant: CH$_2$Cl$_2$). 2.45 g of beige crystals are obtained.

Yield: 77% M.p.: 185° C. Elemental analysis: $C_{14}H_{13}O_3N$ MW=243.26

IR (1% KBr, cm$^{-1}$) 2820, 2220, 1640, 1600–1580, 1440, 1415.

$^1$H NMR (CDCl$_3$, δ ppm) 2.05 (s, 3H, CH3 (3-)); 2.45 (s, 3H, CH$_3$ (2-)); 3.90 (s, 2H, CH$_2$CN); 4.00 (s, 3H, OCH$_3$); 7.00 (d, J$_{6-5}$=9 Hz, 1H, H6); 8.15 (d, J$_{5-6}$=9 Hz, 1H, H5).

STAGE D (2,3-Dimethyl-7-Methoxy-4-Oxo-4H-1-Benzopyran-8-Yl)-Acetic Acid 20 ml of conc. sulphuric acid are added dropwise to a solution of 3.9 g (16.05 mmol) of (2,3-dimethyl-7-methoxy-4-oxo-4H-1-benzopyran-8-yl)-acetonitrile in 20 ml of 50% aqueous acetic acid (v/v). When the addition is complete, the reaction mixture is heated at 70° C. for 4 hours, then cooled and poured onto 150 ml of iced water and left for one night at 5° C. The precipitate that has formed is collected by filtration then dissolved in a 5% sodium hydrogen carbonate solution (heated beforehand to a temperature of between 50° and 60° C). After filtration and acidification of the filtrate with conc. hydrochloric acid, the resulting insoluble material is removed by filtration and then washed 3 times with 50 ml of water each time and dried. 3.70 g of white crystals are obtained.

Yield: 87% M.p.: 211° C. Elemental analysis: $C_{14}H_{14}O_5$ MW=262.26

IR (1% KBr, cm$^{-1}$) 3300–2900, 2820, 1740, 1630, 1610–1580, 1440.

$^1$H NMR (DMSO-d$_6$, δ ppm) 1.90 (s, 3H, CH$_3$ (3-)); 2.40 (s, 3H, CH$_3$ (2-)); 3.70 (s, 2H, CH$_2$COOH); 3.90 (s, 3H, OCH$_3$); 7.20 (d, $J_{6-5}$=9 Hz, 1H, H6); 7.95 (d, $J_{5-6}$=9 Hz, 1H, H5); 12.60 (s, 1H, OH).

STAGE E (7-Methoxy-3-Methyl-4-Oxo-2-Styryl-4H-1-Benzopyran-8-Yl)-Acetic Acid

A solution of sodium methoxide (7.64 mmol; 0,176 g of Na in 30 ml of CH$_3$OH) and then 0.4 ml (3.82 mmol) of benzaldehyde are added, with stirring and with protection from moisture, to 1 g (3.82 mmol) of (2,3-dimethyl-7-methoxy-4-oxo-4H-1-benzopyran-8-yl)-acetic acid dissolved, with the application of heat, in the minimum amount of anhydrous methanol. After having been refluxed for 7 hours, the reaction mixture is poured onto 40 ml of iced water acidified by the addition of conc. HCl. The yellow crystals are dissolved in a 5% solution of sodium hydrogen carbonate, heated beforehand to a temperature of between 50° and 60° C., and then filtered. After acidification of the filtrate with conc. HCl, the insoluble material is removed by filtration and then washed 3 times with 20 ml of water each time and dried. The resulting yellow crystals may or may not be subjected to esterification followed by acid hydrolysis, depending on the degree of purity required.

Yield: 32% M.p.: 282° C. (ethanol) Elemental analysis: $C_{21}H_{18}O_5$, 0.5 H$_2$O MW=359.37 Calculated: C=70.26%, H=5.05%; Found C=70.70%, H=5.00%.

IR (1% KBr, cm$^{-1}$) 3600–3200, 1720, 1630, 1590, 1570, 780 and 685.

$^1$H NMR (DMSO-d$_6$, δ ppm): 2.15 (s, 3H, CH$_3$ (3-)); 3.90 (s, 2H, CH$_2$COOH); 3.95 (s, 3H, OCH$_3$ (7-)); 7.25 (d, Jα-β=16 Hz, 1H, He); 7.75 (d, Jβ-α=16 Hz, 1H, Hβ); 7.20–8.00 (m, 7H, H5 and H6 and H2'-6'); 12.5 (s, 1H, OH).

MS (m/z) 350, 349, 335, 305, 291, 273, 141.

Stages F and G correspond to the purification of (2-styryl-4H-1-benzopyran-8-yl)-acetic acid.

STAGE F (7-Methoxy-3-Methyl-4-Oxo-2-Styryl -4H-1-Benzopyran-8-Yl)-Ethyl Acetate A suspension of 1.80 mmol of (7-methoxy-3-methyl-4-oxo-2-styryl-4H-1-benzopyran-8-yl)-acetic acid in 60 ml of ethanol acidified with 1.5 ml of conc. H$_2$SO$_4$ is heated at the reflux point of the solvent for 7 hours. After having been cooled, the reaction mixture is maintained at 5° C. for several hours and then the precipitate is removed by filtration and dried. Chromatography of the powder on a silica gel column (eluant: CH$_2$Cl$_2$/C$_2$H$_5$OH: 98/2) yields analytically pure yellow crystals.

Yield: 95% Elemental analysis: $C_{23}H_{22}O_5$, MW=378.45 Calculated: C=72.99%, H=5.87%; Found: C=72.76%, H=5.90%.

IR (1% KBr, cm$^{-1}$) 1730, 1620, 1610–1590, 780 and 690.

$^1$H NMR (CDCl$_3$, δ ppm) 1.20 (t, 3H, COOCH$_2$CH$_3$); 2.25 (s, 3H, CH$_3$ (3-)); 3.95 (s, 2H, CH$_2$-COOEt); 4.00 (s, 3H, OCH$_3$ (7-)); 4.20 (q, 2H, COOCH$_2$—CH$_3$); 7.00 (d, $J_{6-5}$=9 Hz, 1H, H6); 7.20–7.65 (m, 7H, Hα, Hβ, H-ar); 8.15 (d, $J_{5-6}$=9 Hz, 1H, H5).

MS (m/z) 350, 349, 335, 305, 291, 273, 141.

STAGE G (7-Methoxy-3-Methyl-4-Oxo-2-Styryl-4H-1-Benzopyran-8-Yl)-Acetic Acid

A suspension of 0.21 mmol of the above ester in a mixture of acetic acid (6 ml) and conc. hydrochloric acid (3 ml) is heated at the reflux point of the solvent for 6 hours. After the reaction mixture has been cooled, 8 ml of water are added and the yellow crystals formed are removed by filtration and dried. Recrystallisation from ethanol yields analytically pure yellow crystals.

EXAMPLE 14

(2-(3,4-Dimethoxystyryl)-7-Methoxy-3-Methyl -4-Oxo-4H-1-Benzopyran-8-Yl)-Acetic Acid Prepared in accordance with the protocol described in Stage(s) E (and optionally F and G) of Example 13.

Yield: 45% M.p.: 240° C. (ethanol) Elemental analysis: $C_{23}H_{22}O_7$, MW=410.45 Calculated: C=67.30%, H=5.41%; Found: C=67.06%, H=5.50%.

IR (1% KBr, cm$^{-1}$) 3600–3200, 1710, 1610, 1595, 1580, 830 and 780.

$^1$H NMR (DMSO-d$_6$, δ ppm) 2.15 (s, 3H, CH$_3$ (3-)); 3.90 (s, 2H, CH$_2$COOH); 3.85 and 3.95 (s, 9H, OCH$_3$ (7-, 3'and 4'-)); 7.05 (d, Jα-β=18 Hz, 1H, Ha); 7.30 (d, Jβ-α=18 Hz, 1H, HD); 7.00–7.45 (m, 4H, H2', 5', 6', and 6); 7.95 (d, $J_{5-6}$=9 Hz, 1H, H5); 12.50 (s, 1H, OH).

EXAMPLE 15

(2-(3,4,5-Trimethoxystyryl)-7-Methoxy-3-Methyl-4-Oxo-4H-1-Benzopyran-8-Yl) -Acetic Acid Prepared in accordance with the protocol described in Stage(s) E (and optionally F and G) of Example 13.

Yield: 42% M.p.: 240° C. (ethanol) Elemental analysis: $C_{24}H_{24}O_8$, 2 H$_2$O MW=476.45 Calculated: C=60.50%, H=5.92%; Found: C=60.40%, H=5.61%.

IR (1% KBr, cm$^{-1}$) 3600–3200, 1720, 1610, 1580, 1570 and 800.

$^1$H NMR (DMSO-d$_6$, δ ppm) 2.15 (s, 3H, CH$_3$ (3-)); 3.70 (s, 2H, CH$_2$COOH); 3.85 and 3.95 (s, 12H, OCH$_3$ (3'-, 4', 5'- and 7-)); 7.05–7.50 (m, 6H, H5 and 6, H2'and 6', H-vinyl); 2.50 (s, 1H, OH).

EXAMPLE 16

(2-(4-Carboxystyryl)-7-Methoxy-3-Methyl-4-Oxo-4H-1-Benzopyran-8-Yl)-Acetic Acid

Prepared in accordance with the protocol described in Stage(s) E (and optionally F and G) of Example 13.

Yield: 40% M.p.: >305° C. (ethanol) Elemental analysis: $C_{22}H_{18}O_7$, MW=394.39 Calculated: C=67.00%, H=4.60%; Found: C=67.76%, H =4.64%.

IR (1% KBr, cm$^{-1}$) 3600–3100, 1710, 1730, 1620, 1590 and 770.

$^1$H NMR (DMSO-d$_6$, δ ppm) 2.15 (s, 3H, CH$_3$ (3-)); 3.90 (s, 2H, CH$_2$COOH); 3.95 (s, 3H, OCH$_3$ (7-)); 7.50 (m, 2H, H2' and 6'); 7.85–8.05 (m, 6H, H3' and 4', H5 and 6, H-vinyl); 12.75 (s, 2H, OH).

PREPARATION 3

8-Methyl-2-Styryl-4H-1-Benzopyran-4-One

STAGE A (2-Hydroxy-3-Methylbenzoyl)-Methylene-Triphenylphosphorane

At room temperature and under a nitrogen atmosphere, 31.25 ml (50 mmol) of a solution of n-BuLi (1.6M in hexane) are added dropwise, with stirring, to 14.6 g (36 mmol) of phosphonium salt suspended in 120 ml of anhydrous tetrahydrofuran. After a contact time of 3 hours, 3 g (18 mmol) of methyl 2-hydroxy-3-methylbenzoate dissolved in 20 ml of tetrahydrofuran are added dropwise to the reaction mixture, which is then heated for 3 hours at a temperature of between 50° and 60° C. and subsequently filtered. Evaporation of the solvents yields 5.9 g of yellow crystals recrystallised from methanol.

Yield: 80% M.p.: 170° C. Elemental analysis: C$_{27}$H$_{23}$O$_2$P MW=410.46 Calculated: C=79.01%, H=5.65%; Found: C=79.02%, H=5.61%.

IR (1% KBr, cm$^{-1}$) 3400, 1590, 1540, 750, 720 and 690.

$^1$NMR (CDCl$_3$, δ ppm) 2.20 (s, 3H, CH$_3$ (3-)); 6.65 (t, J$_{5-6}$=J$_{5-4}$=7 Hz, 1H, H5); 7.15 (d., J$_{4-5}$=7 Hz, 1H, H4); 7.35–7.80 (m, 18H, PPh$_3$, H6, HC=P and OH).

STAGE B

8-Methyl-2-Styryl-4H-1-Benzopyran-4-One

Under a nitrogen atmosphere, 2 g (4.87 mmol) of (2-hydroxy-3-methylbenzoyl)-methylenetriphenylphosphorane and 2.43 g (14.6 mmol) of cinnamoyl chloride in 200 ml of anhydrous pyridine are stirred and heated at 60° C. for 24 hours. After removal of the pyridine, the residue is taken up in dichloromethane and extracted with an aqueous 1N sodium hydroxide solution and then with a saturated aqueous solution of NaCl until neutral. Removal of the dichloromethane results in 1 g of a brownish oil which, on crystallisation in methanol, yields 0.6 g of fine yellow crystals.

Yield: 60% M.p.: 152° C. Elemental analysis: C$_8$H$_{14}$O$_2$, MW=262 Calculated: C=82.44%, H=5.34%; Found: C=82.22%, H=5.44%.

IR (1% KBr, cm$^{-1}$) 1640, 1610 and 1600.

$^1$H NMR (CDCl$_3$, δ ppm) 2.60 (s, 3H, CH$_3$ (8-)); 6.30 (s, 1H, H3); 6.80 (d, Jα-β=16 Hz, 1H, Hα); 7.20–7.65 (m, 8H, H6 and 7, Hβ, H2'to 6'); 8.05 (dd, J$_{5-6}$=7.5 Hz, J$_{5-7}$=2.0 Hz, 1H, H5).

MS (m/z) 262, 261, 245, 155, 134, 128, 106, 77.

EXAMPLE 17

3,8-Dimethyl-2-Styryl-4H-1-Benzopyran-4-One

STAGE A (1-(2-Hydroxy-3-Methylbenzoyl)-Ethylidene)-Triphenylphosphorane

Prepared in accordance with the protocol described in Stage A of Preparation 3.

Yellow crystals.

Yield: 51% M.p.: 150° C. Elemental analysis: C$_{28}$H$_{25}$O$_2$P, MW=424.45 Calculated: C=79.23%, H=5.94%; Found: C=79.22%, H=5.90%.

IR and $^1$H NMR: refer to Tables I and II.

STAGE B 6,8-Dimethyl-2-Styryl-4H-1-Benzopyran-4-One

Prepared in accordance with the protocol described in Stage B of Preparation 3, replacing the (2-hydroxy-3-methyl-benzoyl)-methylenetriphenylphosphorane with (1-(2-hydroxy-3-methylbenzoyl)-ethylidene)-triphenylphosphorane.

Orange crystals.

Yield: 67% M.p.: 136° C. (methanol) Elemental analysis: C$_{19}$H$_{16}$O$_2$, MW=276.33 Calculated: C=82.58%, H=5.83%; Found: C=82.43%, H=5.74%.

IR and $^1$H NMR: refer to Tables III and IV.

EXAMPLE 18

8-Allyl-2-Styryl-4H-1-Benzopyran-4-One

STAGE A

Methyl 3-Allyl-2-Hydroxybenzoate

With protection from moisture, 10 g (66 mmol) of methyl salicylate dissolved in 10 ml of anhydrous DMF are added dropwise, with stirring at 60° C. to a suspension of sodium hydride (74 mmol) in 60 ml of anhydrous DMF. The temperature is maintained for a period of 2 hours after the addition has been completed; 6 ml (70 mmol) of allyl bromide are then added dropwise to the reaction mixture, which is again heated for 2 hours. After excess sodium hydride has been decomposed by the addition of methanol, the reaction mixture is diluted with 50 ml of ethyl ether and then poured onto 100 ml of iced water. After extraction of the aqueous phase with ethyl ether, the combined organic phases are washed with an aqueous 1N sodium hydroxide solution and then with a saturated aqueous solution of NaCl and finally dried over sodium sulphate. Removal of the solvents results in an orange oil which is heated at 250° C. for 30 minutes. Purification by distillation in vacuo yields 11.44 g of colourless oil.

Yield: 90% B.P.0.5 mmHg: 115°–120° C. Elemental analysis: C$_{11}$H$_{12}$O$_3$, MW=192.2

IR (1% KBr, cm$^{-1}$) 3300–3200, 2820, 1680.

$^1$H NMR (CDCl$_3$, δ ppm) 3.45 (d, J=6.5 Hz, 2H, CH$_2$—CH=CH$_2$); 3.90 (s, 3H, OCH$_3$); 5.00–5.15 (dd, J=16 Hz, 2H, CH=$\underline{CH_2}$); 5.80–6.15 (m, 1H, CH$_2$—$\underline{CH}$=CH$_2$); 6.75–7.75 (m, 3H, H4,5,6); 11.05 (s, 1H, OH).

STAGE B (3-Allyl-2-Hydroxybenzoyl)-Methyl-Triphenylphosphorane

Prepared in accordance with the protocol described in Stage A of Preparation 3.

Orange crystals.

Yield: 77% M.p.: 176° C. Elemental analysis: C$_{29}$H$_{25}$O$_2$P, MW=436.45 Calculated: C=79.81%, H=5.77%; Found: C=79.99%, H=5.96%.

IR and $^1$H NMR: refer to Tables I and II.

STAGE C

8-Allyl-2-Styryl-4H-1-Benzopyran-4-One

Prepared in accordance with the protocol described in Stage B of Preparation 3.

Beige crystals.

Yield: 50% M.p.: 142° C. (methanol) Elemental analysis: $C_{20}H_{16}O_2$, MW=288.36 Calculated: C=83.31%, H=5.89% Found: C=83.45%, H=5.75%.

IR and $^1H$ NMR: refer to Tables III and IV.

EXAMPLE 19

8-Allyl-3-Methyl-2-Styryl-4H-1-Benzopyran-4-One

STAGE A (1-(3-Allyl-2-Hydroxybenzoyl)-Ethylidene)-Triphenylphosphorane

Prepared in accordance with the protocol described in Stage B of Example 18, replacing methyltriphenylphosphonium iodide with ethyltriphenylphosphonium iodide.

Yellow crystals.

Yield: 54% M.p.: 152° C. Elemental analysis: $C_{30}H_{27}O_2P$, MW=450.52 Calculated: C=79.98%, H=6.04%; Found: C=79.55%, H=6.06%.

IR and $^1H$ NMR: refer to Tables I and II.

STAGE B

8-Allyl-3-Methyl-2-Styryl-4H-1-Benzopyran-4-One

Prepared in accordance with the protocol described in Stage B of Preparation 3.

White crystals.

Yield: 60% M.p.: 126° C. (methanol) Elemental analysis: $C_{21}H_{18}O_2$, MW=302.37 Calculated: C=83.42%, H=6.00%; Found: C=82.79%, H=6.07%.

IR and $^1H$ NMR: refer to Tables III and IV.

EXAMPLES 20 AND 21

6-Methoxy-8-Allyl-2-Styryl-4H-1-Benzopyran-4-One (Example 20)

8-Propyl-2-Styryl-4H-1-Benzopyran-4-One (Example 21)

The above compounds are obtained by replacing the (3-allyl-2-hydroxybenzoyl)-methyltriphenylphosphorane in Stage C of Example 18 with:

on the one hand (Example 20) (3-allyl-2-hydroxy-5-methoxybenzoyl)-methylenetriphenylphosphorane $C_{30}H_{27}O_3P$, MW=466.47, the physical characteristics of which are as follows:

yellow crystals M.p.: 186° C.

IR and $^1H$ NMR: refer to Tables I and II;

and on the other hand (Example 21) (2-hydroxy-3-propyl)-methylenetriphenylphosphorane $C_{29}H_{27}O_2P$, MW=438.45 obtained as in Stage B of Example 18 from methyl 2-hydroxy-3-propylbenzoate and of which the physical characteristics are as follows:

yellow crystals M.p.: 142° C.

IR and 1H NMR: refer to Tables I and II.

EXAMPLE 20

White crystals

Yield: 70% M.p.: 132° C. (methanol) Elemental analysis: $C_{21}H_{18}O_3$, MW=318.37 Calculated: C=79.15%, H =5.65%; Found: C=79.40%, H =5.74%.

IR and 1H NMR: refer to Tables III and IV.

EXAMPLE 21

White crystals

Yield: 70% M.p.: 129° C. (methanol) Elemental analysis: $C_{20}H_{18}O_2$, MW=290.36 Calculated: C=80.24%, H=6.40% Found: C=79.86%, H=6.29%.

IR and 1H NMR: refer to Tables III and IV.

TABLE 1

IR($CM^{-1}$) SPECTRAL CONSTANTS OF (2-HYDROXYBENZOYL)-METHYLENE (ETHYLIDENE) TRIPHENYLPHOSPHORANES

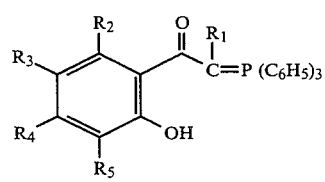

| N° | EXAMPLES | $\nu$OH | $\nu$C=O | $\nu$C=C | $\gamma$C=H | $\nu$C—P |
|---|---|---|---|---|---|---|
| 17 | $R_1 = R_5 = CH_3$, $R_2 = R_3 = R_4 = H$; | 3200 | 1580 | 1520 | 760 and 700 | 690 |
| 18 | $R_1 = R_2 = R_3 = R_4 = H$, $R_5 = CH_2—CH=CH_2$; | 3500 | 1595 | 1570 | 750 and 720 | 700 |
| 19 | $R_1 = CH_3$, $R_5 = CH_2—CH=CH_2$, $R_2 = R_3 = R_4 = H$; | 3200 | 1600 | 1580 | 750 and 730 | 700 |
| 20 | $R_1 = R_2 = R_4 = H$, $R_3 = OCH_3$, $R_5 = CH_2—CH=CH_2$; | 3300 | 1610 | 1590 | 850 | 700 |
| 21 | $R_1 = R_2 = R_3 = R_4 = H$, $R_5 = CH_2CH_2CH_3$; | 3200 | 1610 | 1600 | 750 and 720 | 695 |

TABLE II $^1H$ NMR SPECTRAL CONSTANTS OF (2-HYDROXYBENZOYL)-METHYLENE (ETHYLIDENE) TRIPHENYLPHOSPHORANES (100 MHz, $CDCl_3$, δ ppm)

| N° EXAMPLES | | $R_1$ | $R_2$ | $R_3$ | $R_4$ | $R_5$ |
|---|---|---|---|---|---|---|
| 19 | $R_1 = R_5 = CH_3$, $R_2 = R_3 = R_4$ H; | 1,90 (d) $^3J_{H-P} = 18$ Hz | 7,30–7,80* (m) | 2,20 (s) | 7,30–7,80* (m) | 7,30–7,80* (m) |
| 20 | $R_1 = R_2 = R_3 = R_4 =$ H, | 7,00 | 7,80–7,45* | 6,00 (1H, m) | 7,20 | 6,80 |

TABLE II-continued

¹H NMR SPECTRAL CONSTANTS OF (2-HYDROXYBENZOYL)-METHYLENE (ETHYLIDENE) TRIPHENYLPHOSPHORANES (100 MHz, CDCl₃, δ ppm)

| N° EXAMPLES | $R_1$ | $R_2$ | $R_3$ | $R_4$ | $R_5$ |
|---|---|---|---|---|---|
| $R_5 = CH_2—CH=CH_2$ $^2J_{H-P} = 32.4$ Hz | (d) | (m) | 5,05 (2H, d.d., J = 16 Hz) 3,40 (2H, d.e., J = 7 Hz) | (d.e.) $J_{4-5} = 7$ Hz | (t) $J_{5-6} = 8$ Hz |
| 21 $R_1 = CH_3, R_5 = CH_2$ — $CH=CH_2$, $R_2 = R_3 = R_4 = H$; $^3J_{H-P} = 17$ Hz | 1,85 (d) | 7,70–7,50* (m) | 6,00 (1H, m) 5,10 (2H, d.d., J = 16 Hz) 3,35 (2H, d.e., J = 6 Hz) | 7,70–7,50* (m) | 7,70–7,50* (m) |

*Protons situated in a complex area

TABLE III

IR(cm⁻¹) SPECTRAL CONSTANTS OF 2-STYRYL-4H-1-BENZOPYRAN-4-ONES
($R_6 = R_7 = R_8 = H$)

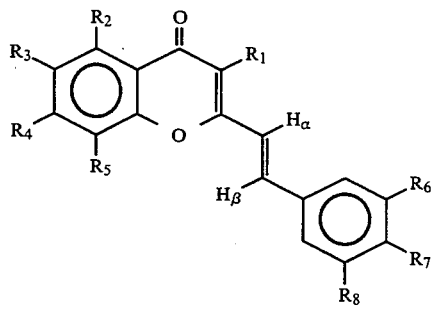

| N° EXAMPLES | νC=O | νC=C |
|---|---|---|
| 17 $R_1 = R_5 = CH_3$, $R_2 = R_3 = R_4 = H$; | 1630 | 1610 and 1600 |
| 18 $R_1 = R_2 = R_3 = R_4 = H$, $R_5 = CH_2—CH=CH_2$; | 1630 | 1600 and 1590 |
| 19 $R_1 = CH_3, R_5 = CH_2—CH=CH_2$, $R_2 = R_3 = R_4 = H$; | 1620 | 1595 and 1580 |
| 20 $R_1 = R_2 = R_4 = H$, $R_3 = OCH_3, R_5 = CH_2—CH=CH_2$; | 1630 | 1600 and 1580 |
| 21 $R_1 = R_2 = R_3 = R_4 = H$, $R_5 = CH_2CH_2CH_3$; | 1620 | 1610 and 1590 |

TABLE IV

¹H NMR SPECTRAL CONSTANTS OF 2-STYRYL-4H-1-BENZOPYRAN-4-ONES (100 MHZ, CDCl₃, δ ppm)

| N° EXAMPLES | $R_1$ | R2 | R3 | R4 | R5 | Hα | Hβ | H-ar |
|---|---|---|---|---|---|---|---|---|
| 17 $R_1 = R_5 = CH_3$, $R_2 = R_3 = R_4 = H$; | 2,25 (s) | 8,15 (d.d.) $J_{5-6} = 7,5$ Hz $J_{5-7} = 2,0$ Hz | 7,70–7,15* (m) | | 2,60 (s) | 7,25 (d) Jα-β = 16 Hz | | 7,70–7,15* (m) |
| 18 $R_1 = R_2 = R_3 = R_4 = H$, $R_5 = CH_2—CH=CH_2$; | 6,35 (s) | 8,10 (d.d.) $J_{5-6} = 8$ Hz $J_{5-2} = 2$ Hz | 7,70–7,25* (m) | | 3,75 (2H, d., J = 6,4 Hz) 5,20 (2H, d.d., J = 16 Hz) 6,25–5,95 (1H, m) | 6,80 (d) Jα_β = 16 Hz | 7,40 (d) Jα-β = 16 Hz | 7,70–7,25* (m) |
| 19 $R_1 = CH_3, R_5 = CH_2$— $CH=CH_2$, $R_2 = R_3 = R_4 = H$; | 2,25 (s) | 8,15 (d.d.) $J_{5-6} = 8$ Hz $J_{5-7} = 2$ Hz | 7,60–7,25* (m) | | 3,75 (2H, d., J = 6,2 Hz) 5,25 (2H, d.d., J = 16 Hz) 6,30 (1H, m) | 7,30 (d) Jα-β = 16 Hz | 7,50 (d) Jβ-α = 16 Hz | 7,60–7,25* (m) |
| 20 $R_1 = R_2 = R_4 = H$, $R_3 = OCH_3, R_5 = CH_2—CH=CH_2$ | 6,35 (s) | 7,65–7,15* (m) | 3,90 (s) | 7,65–7,15* (m) | 3,70 (2H, d., J = 6,3 Hz) 5,30 (2H, d.d., J = 16 Hz) 6,10–5,95 (1H, m) | 6,35 (d) Jα-β = 16 Hz | 7,40 (d) Jβ-α = 16 Hz | 7,65–7,15* (m) |
| 21 $R_1 = R_2 = R_3 = R_4 = H$, $R_5 = CH_2 CH_2CH_3$; | 6,35 (s) | 8,05 (d.d.) $J_{5-6} = 8,0$ Hz $J_{5-7} = 2$ Hz | 8,05–7,25* (m) | | 2,95 (2H, t., J = 7 Hz) 1,80 (2H, m, J = 7 Hz) 1,05 (2H, t, J = 7 Hz) | 6,80 (d) Jα-β = 16 Hz | | 8,05–7,25* (m) |

*Protons situated in a complex area

PHARMACOLOGICAL STUDY:

EXAMPLE 22

Growth Inhibition of Cell Line L1210

The growth of this leukaemia cell line in mice is assessed by the capacity of the cells to incorporate tritiated thymidine. The rate of incorporation is measured 24 hours after the introduction of the test compound into the culture medium.

Table V lists, for each compound, the concentration that inhibits cell growth by 50%.

TABLE V

| EXAMPLE N° | IC₅₀ (μM) 24 hours | EXAMPLE N° | IC₅₀ (μM) 24 hours |
|---|---|---|---|
| 1 | 12,50 | 17 | 7,50 |
| 2 | 6,40 | 18 | 5,85 |
| 3 | 5,00 | 19 | 6,60 |
| 4 | 12,00 | 20 | 3,00 |
| | | 21 | 7,25 |
| 7 | 8,50 | | |
| Reference : | | Retinoic acid | 20,05 |

This study shows that the activity of the Examples studied is superior to that of retinoic acid.

EXAMPLE 23

Anti-Tumour Activity on Colon C38 Adeno-Carcinoma In Vivo

After subcutaneous implantation of a fragment of tumour (colon 38) in the axillary region, on the 2nd and 4th days after implantation a solution of the test compound is administered to a group of animals by the intraperitoneal route. On the 20th day the animals are sacrificed and the tumour volume is ascertained.

The % T/C ratio is calculated as follows:

$$\frac{T}{C} = \frac{\text{volume of the tumours, experimental group}}{\text{volume of the tumours, control group}} \times 100$$

Table VI lists the T/C values obtained for some compounds.

TABLE VI

| EXAMPLE N° | Tumour volume (mm3) after 20 days | T/C % |
| --- | --- | --- |
| 1 | 573 | 56% |
| 2 | 356 | 35% |
| Control | 1027 | — |

EXAMPLE 24

Cell Differentiation

The cell differentiation is determined according to the method of J. M. GALLUP and al. (Proceedings of the Society for Experimental Biology and Medecine, 186, 269–274, 1987).

HL-60 cells (human promyclocyte) ($2 \times 10^5$ cells/ml) are incubated during six days with the tested compounds. An aliquot (0,5 ml) of cells is than incubated with 0,5 ml of a 0,2% NBT (Nitroblue Tetrazolium) solution and 200 mg/ml of PMA (phorbol ester) for 20 min at 37° C.

Cells are washed with PBS and numbered under microscope, Table VII lists the percentage of cells containing cristals of reduced NBT (i,e, % of positive NBT cells) at the concentration of 20 μM.

TABLE VII

| Example N° | % of positive NBT cells |
| --- | --- |
| 1 | 52 |
| 2 | 85 |
| 3 | 59 |
| 19 | 45 |

EXAMPLE 25

Example of a Pharmaceutical Composition 5 mg tablet from a formula for the preparation of 1000 tablets:

| | |
| --- | --- |
| 6-methoxy-8-allyl-2-styryl-4H-1-benzopyran-4-one | 5 g |
| wheat starch | 20 g |
| cornstarch | 20 g |
| lactose | 75 g |
| magnesium stearate | 2 g |
| silica | 1 g |
| hydroxypropylcellulose | 2 g |

We claim:

1. A method of treating an animal or human living body afflicted with an adenocarcinoma cancer susceptible to such treatment comprising the step of administering to the said living body an amount of a compound selected from those of Formula (I):

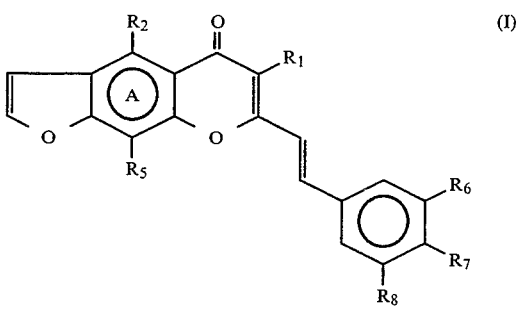

in which:

$R_1$ represents hydrogen, two or three of $R_6$, $R_7$, and $R_8$ being methoxy, and any other being hydrogen; each of $R_2$ and $R_5$, which may be the same or different, represents hydrogen or methoxy, its enantiomers and diastereoisomers which is effective for amelioration of the said cancer.

2. A method of claim 1, wherein the compound is administered in combination with a pharmaceutically acceptable excipient vehicle.

3. A method of claim 1, in which the configuration of the double bond of the styryl group is (E).

4. The method of claim 1, wherein the compound is selected from 4-methoxy-7-(3,4-dimethoxystyryl)-5H-furo[3,2-g]benzopyran-5-one, and its enantiomers and diastereoisomers.

5. A method of claim 1 wherein the compound is selected from 4-methoxy-7-(3,4,5-trimethoxystyryl)-5H-furo[3,2-g]benzopyran-5-one and its enantiomers and diastereoisomers.

* * * * *

UNITED STATES PATENT AND TRADEMARK OFFICE
CERTIFICATE OF CORRECTION

PATENT NO. : 5,409,952

DATED : April 25, 1995

Page 1 of 2

INVENTOR(S) : Jean D. Brion, Guillaume Le Baut, Francoise Zammattio, Alian Pierre, Ghanem Atassi, Larbi Belchmi It is certified that error appears in the above-indentified patent and that said Letters Patent is hereby corrected as shown below:

TITLE PAGE, ITEM [75], Inventors: line 3; "Zammatio" should read -- Zammattio --

Column 3, line 36; delete the "I" and change the "and Rll" to -- and $R_{11}$ --

Column 3, line 42; "P⊕($C_6H_5$)$_3$X⊖" should read -- P⊕($C_6H_5$)$_3$X⊖ --; also move the "(IV)" to the end of the line so as to identify the formula, not read as part of the formula.

Column 3, line 46; "X⊖" should read -- X⊖ --

Column 6, line 52; "4H" should read -- 4H— --

Column 7, line 28; "-1Benzopyran-6-" should read -- -1-Benzopyran-6- --

Column 10, line 64; "($CDCl_3$,ppm)" should read -- ($CDCl_3$,δppm) --

Column 13, line 36; "Yl" should read -- yl --

Column 13, line 45; "CH2COOH);" should read -- $CH_2COOH$); --

Column 14, line 7; "CH3" should read -- $CH_3$ --

Column 14, line 8; (d, J8-6" should read -- (d, $J_{8-6}$ --

Column 14, line 29; "CH3" should read -- $CH_3$ --

Column 14, line 54; "CH3" should read -- $CH_3$ --

Column 15, line 22; "0,176" should read -- 0.176 --

Column 15, line 48; "He" should read -- Ha --

Column 16, line 7; "COOCH2$CH_3$" should read -- $COOCH_2CH_3$ --

Column 16, line 8; insert "$_2$—$CH_3$" at the end of the line to make it read -- $COOCH_2$—$CH_3$ --

Column 16, line 9; delete "$_2$—$CH_3$" at the beginning of the line.

Column 16, line 38; "HD)" should read -- Hβ) --

Column 16, line 55; "(3'-,4',5'- and 7-));" should read -- (3'-,4'-,5'- and 7-)); --

UNITED STATES PATENT AND TRADEMARK OFFICE
CERTIFICATE OF CORRECTION

PATENT NO. : 5,409,952

DATED : April 25, 1995

INVENTOR(S) : Jean D. Brion, Guillaume Le Baut, Francoise Zammattio, Alian Pierre, Ghanem Atassi, Larbi Belchmi It is certified that error appears in the above-indentified patent and that said Letters Patent is hereby corrected as shown below:

Column 17, line 29; "$^1$NMR" should read -- $^1$H NMR --
Column 20, line 23; "1H" should read -- $^1$H --
Column 20, line 30; "1H" should read -- $^1$H --
Column 20, line 37; "1H" should read -- $^1$H --
Column 20, Table II; second line under examples "$R_2=R_3=R_4H$;" should read -- $R_2=R_3=R_4=H$; --
Column 21, Table II; second line under examples "$CH_2$" should read -- $CH_2-$ --
Column 21, Table II; third line under examples delete the "-"
Column 23, line 25; "microscope," should read -- microscope. --

Signed and Sealed this

Fifteenth Day of August, 1995

Attest:

BRUCE LEHMAN

Attesting Officer　　Commissioner of Patents and Trademarks